United States Patent [19]

Genter et al.

[11] Patent Number: 4,470,307
[45] Date of Patent: Sep. 11, 1984

[54] SONIC SYSTEM INSPECTION CONTROL

[75] Inventors: Wayne L. Genter; Frank Pedatella, both of Lower Burrell; Philip M. Kasprzyk, Allegheny Township, Armstrong County, all of Pa.

[73] Assignee: Aluminum Company of America, Pittsburgh, Pa.

[21] Appl. No.: 391,522

[22] Filed: Jun. 24, 1982

[51] Int. Cl.³ .............................................. G01N 29/04
[52] U.S. Cl. ........................................ 73/634; 73/644; 73/1 DV
[58] Field of Search .............. 73/634, 644, 1 DV, 631

[56] References Cited

U.S. PATENT DOCUMENTS

| | | | |
|---|---|---|---|
| 3,678,736 | 7/1972 | May | 73/634 |
| 3,969,926 | 7/1976 | Walker et al. | 73/634 |
| 3,978,714 | 9/1976 | Shraiber et al. | 73/634 |
| 3,981,184 | 9/1976 | Matay | 73/67.8 S |
| 4,043,185 | 8/1977 | Siebert | 73/67.7 |

FOREIGN PATENT DOCUMENTS 523348  11/1976  U.S.S.R. ................ 73/634

*Primary Examiner*—Anthony V. Ciarlante
*Attorney, Agent, or Firm*—Elroy Strickland

[57] ABSTRACT

Method and apparatus for maintaining parallel relationship between the working face of a sound transducer and a planar surface of a workpiece or object under examination by the transducer, and for measuring and adjusting the thickness of a layer of liquid located between the transducer and object. A calibrating method and circuit is also associated with the transducer. Included is the step of placing the working face of the transducer in a position that is adjacent to but spaced from a front planar surface of the object, and providing the layer of liquid between the two. The transducer is then energized such that sound energy is directed into and reflected from the object after passing through the layer of liquid, the sound energy reflected from the object being received at the working face of the transducer. In response thereto the transducer produces a train of electrical pulses that are integrated to provide an analogue signal that is proportional to the total amount of sound energy received by the transducer from the object, the amount of energy received being maximum when the face of the transducer and the planar surface of the object are parallel to each other. The analogue signal is then used to maintain the parallel relationship between the working face of the transducer and the planar surface of the object.

12 Claims, 4 Drawing Figures

SONIC SYSTEM INSPECTION CONTROL

BACKGROUND OF THE INVENTION

The present invention relates generally to sonic examination of workpieces and other objects, and particularly to an automated system that maintains parallel relationship between the working face of a sound transducer and the planar surface of a workpiece.

In using sonic and ultrasonic energy to examine a workpiece for discontinuities that may be in the workpiece, it is desirable to maintain the face of the transducer that directs the sound energy into the workpiece in parallel relationship with the workpiece. In this manner the transducer receives a amaximum amount of energy reflected from the workpiece in the examination process. The receipt of a maximum signal from the workpiece under examination insures a correct reading of the internal structure and integrity of the workpiece. It can be appreciated that if the transducer and associated examining circuitry are not receiving the best possible signal from the workpiece, the results of the examination are compromised.

In U.S. Pat. No. 4,043,185 to Siebert, ultrasonic examining heads are maintained parallel with a plate or sheet being examined by physically disposing the heads on and in physical contact with the sheet, using low friction pads in contact with the sheet. A mechanically pivotal linkage structure supports the heads. Such means have certain disadvantages in that the readings provided by the heads may be affected by uneven surface conditions of the sheet. Similarly, movement of the heads and linkage, after a period of time and use, might cause wear at the linkage joints such that erroneous readings (again) might be the result. Further, it is preferred that a water path be provided and maintained between the examining heads and the surface of the object under examination, the water path providing a mechanism for coupling the sound energy into the object under examination that is not affected by surface conditions of the workpiece or object. And lastly, any physical contact with the workpiece offers the opportunity for scratching or otherwise damaging or marking the workpiece surface.

BRIEF SUMMARY OF THE INVENTION

The present invention is directed to a method of and means for maintaining parallel relationship of one or more transducers and a workpiece or object under examination having a planar surface while the transducer is spaced from the workpiece so that a water (or other liquid) path of constant distance is provided between the workpiece and the transducer. This is accomplished by rotating the transducer about two mutually perpendicular axes that are parallel with the planar surface of the workpiece. The transducer is rotated in response to the magnitude of a video signal representing the output of the transducer.

More particularly, circuitry is provided to receive and amplify the output of the transducer, and to provide a video signal for an oscilloscope so that the signal received by the transducer can be visually observed. The video signal is in the fom of discrete spikes or pulses which are, in addition, integrated to provide an analogue signal that is proportional to the total amount of energy received by the transducer from the workpiece. The amount of reflected energy and thus the magnitude of the integrated video signal are maximum when the working face of the transducer and the planar surface of the workpiece are essentially parallel to each other. A digital computer circuit is provided which converts the analogue signal to digital form, and in response thereto, outputs a signal that is employed to control the angular position of the transducer with respect to the planar surface of the workpiece. The computer maintains the parallel relationship based upon receipt of the maximum analogue signal, as the transducer is moved along the workpiece, for example,, to examine the entire structure thereof. In this manner, the system and method assure parallel relationship between the transducer and workpiece which, in turn, insures a complete and accurate inspection of the workpiece.

The above system and process are particularly useful in the examination of aluminum plate for the aircraft industry. The aircraft industry requires high quality plate for its aircraft for obvious reasons. The system of the present invention insures that the examination procedure of the plate is accurate, rapid and efficient. The accuracy of the system is established by use of a calibration procedure involving a standard test object, the accuracy of which is known and predetermined by controls established by the National Bureau of Standards. Before using the transducer and the system, the transducer is positioned over the test object and the gain of the system is adjusted to match that of the known, predetermined response of the test object.

This adjustment can be automatically made by a second computer, such as a microcomputer employed in the process of examining the plate for discontinuities. The computer has stored therein the value of the response of the test object. The computer compares this response to that of the output of the transducer and its associated circuitry when sonic energy is directed to the test object, and adjusts the gain of the circuitry until the two responses are the same.

THE DRAWINGS

The invention, along with its advantages and objectives, will be best understood from the following detailed description and the accompanying drawings in which.

Figure 4:
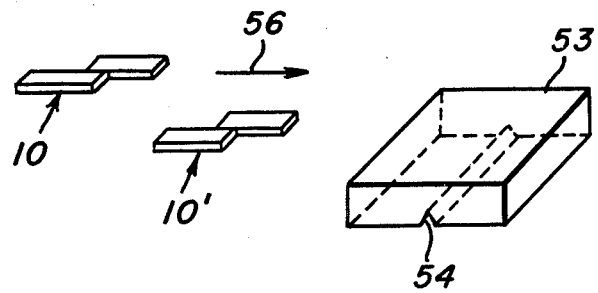
Figure 3:
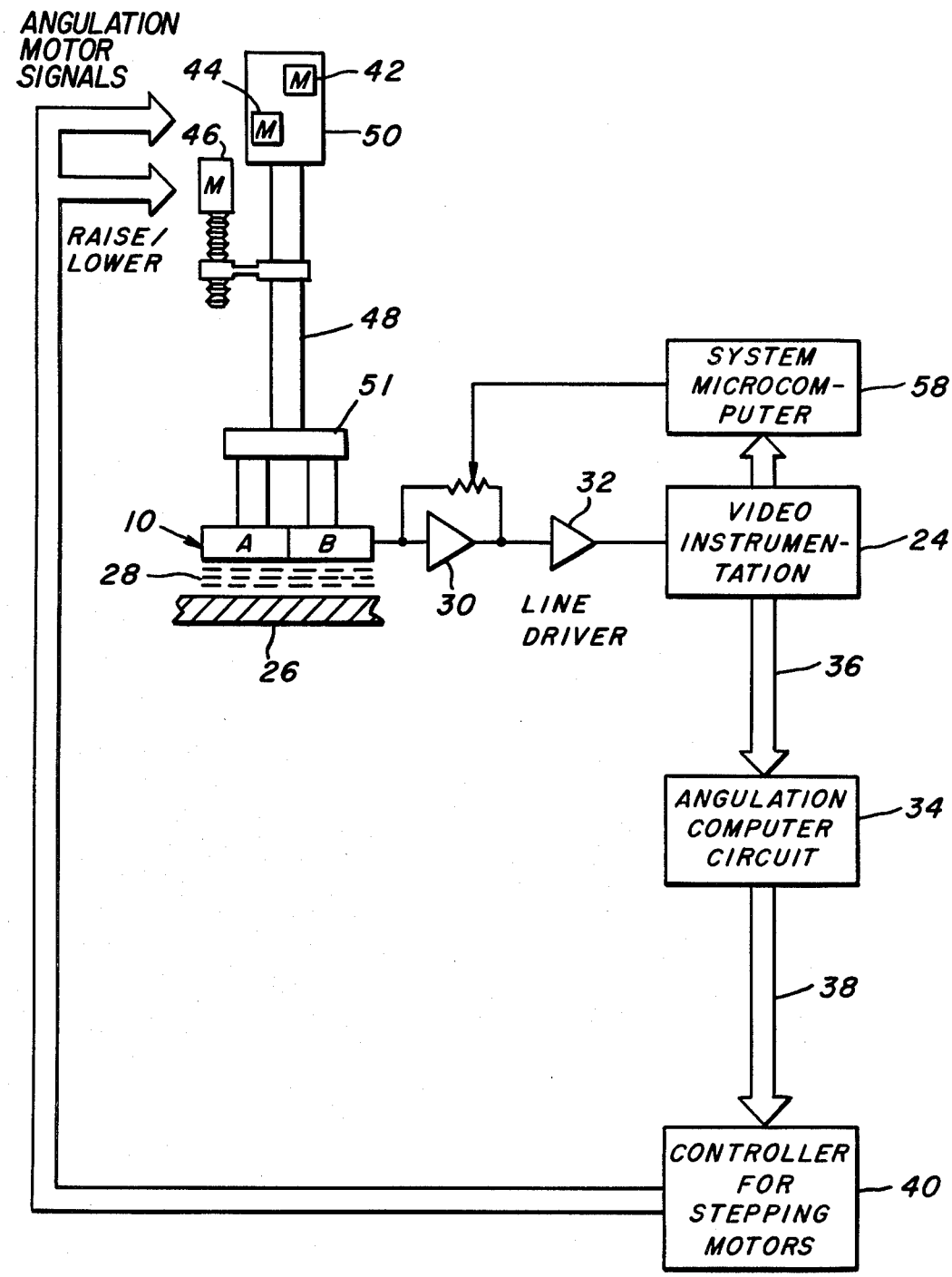

FIG. 3 is a schematic diagram showing the inspection system of the invention in which the above integrated video and a time duration of water path signal are used to adjust the position of transducers employed in the inspection process; in addition, FIG. 3 shows schematically means for automatically calibrating the system; and FIG. 4 is a plan view of four transducers, schematically represented, for examining a plate or sheet of material and for being calibrated by using a test object.

PREFERRED EMBODIMENT

Figure 1:
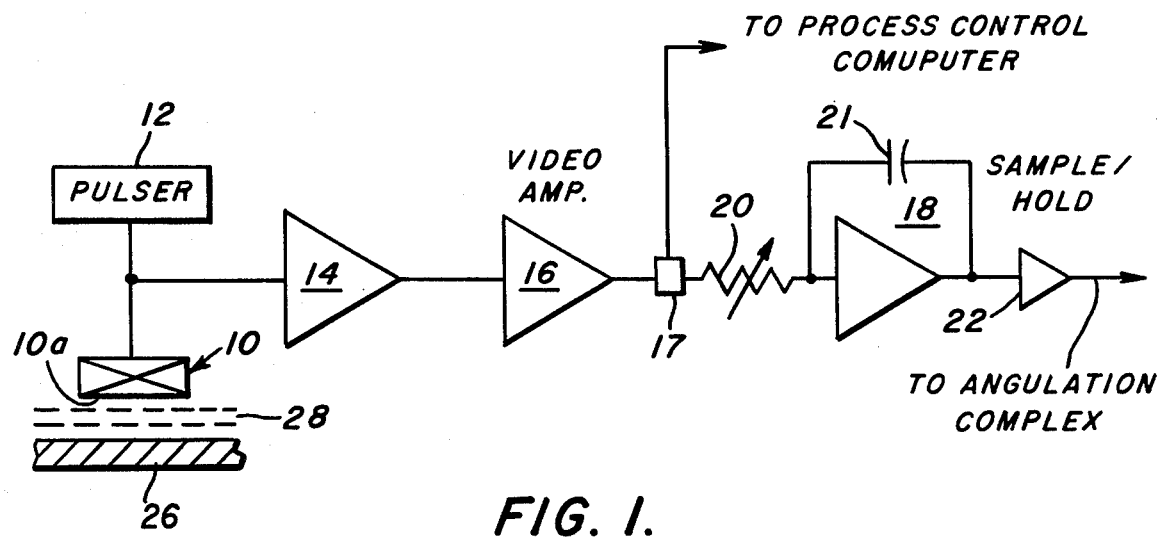
FIG. 1 is a schematic diagram of a video integrating circuit employed in the present invention.

Referring now to FIG. 1 of the drawings, a sound (sonic) transducer 10 is shown schematically, the transducer being electrically connected to a pulsing circuit 12 and to a radio frequency amplifier 14. The pulsing and amplifying circuits of the invention are electrically isolated in a well-known manner. If 10 is representative of two transducers to be energized at the same time, the pulsing and amplifying arrangement can be that of the disclosure of U.S. application Ser. No. 333,706 filed Dec. 23, 1981, though the present invention is not limited thereto.

The output of amplifier 14 is connected to the input of a video amplifier 16. The output of 16 is connected to a detector circuit 17 and then to an integrating circuit 18 through a variable resistor 20. 20 is employed to set the gain of 16. 14, 16, 17 and 18 are typical high frequency amplifiers having appropriate inputs, gain control resistors and feedback elements. These have not been shown in the drawings to avoid undue complication. 18, however, is shown with a feedback capacitor 21 to provide an integrating function described below.

The output of the video integrator is connected to the input of a circuit 22 that holds, as explained in detail hereinafter, the integrated output of 18.

Amplifiers 14 and 16, and video integrator and sample hold devices 18 and 22 are part of an instrument and panel 24 (only schematically represented in FIG. 3) providing, inter alia, horizontal and vertical deflection of the video signal so that the signal can be visually observed on a cathode ray tube (not shown) of the instrument. Gain control 20 is a part of the instrument and thereby available for adjustment by operating personnel.

The operation of the circuit means thus far described is as follows. Pulser 12 energizes transducer 10 by directing to it repetitive pulses of electrical energy. The pulses cause the transducers to vibrate at the resonant frequency of the transducer, which frequency is that of a sound or sonic (or ultrasonic) frequency. The energy of the sound is radiated from a working face thereof, such as face 10a in FIG. 1.

The sound energy produced by the transducer is coupled to a workpiece 26 via a layer of liquid 28 such as water. When the energy reaches the front or upper surface of the workpiece, a narrow (time wise) pulse of sound energy is reflected from the front surface and directed back to the working face of the transducer. This occurs after the cessation of the electrical pulse that energized the transducer. The transducer converts the sound pulse it receives from the front surface of the workpiece to an electrical pulse. This pulse is amplified by suitable amplifying means, designated generally by numeral 30 in FIG. 3, and directed via a "line driver" 32 (which maintains signal strength in the face of any losses occurring in connecting cables, etc.) to amplifier 14 in instrument 24. The structures of 30 and 14 provide stages of amplification sufficient for the purposes of video detection and integration, presently to be explained. The amplified pulse is the first pulse of the A series of pulses represented pictorially in FIG. 2. These can be viewed on the cathode ray tube (not shown) of instrument 24.

Figure 2:
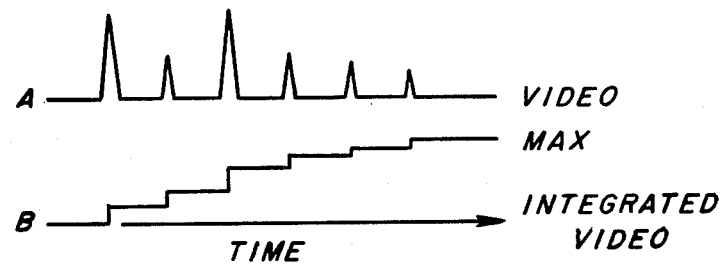
FIG. 2 shows respectively a train of consecutive video pulses, and a curve representing the result of the integration and summation of the areas of the pulses.

The sonic energy directed to the workpiece 26 penetrates the workpiece. When the energy reaches the rear or lower surface of 26, the energy is reflected back through the workpiece and through the layer of water 28 to the transducer. The transducer again outputs a pulse of electrical energy in response to the sound energy reflected from the rear surface of 26, which pulse is again amplified and presented to 18. In FIG. 2, this pulse is represented by the third spike in the series of A pulses.

The first and third pulses in FIG. 2 have an amplitude that is larger than a second, intermediate pulse. This intermediate spike is shown in FIG. 2 to indicate a minute discontinuity in workpiece 26.

Trailing the third video pulse in FIG. 2 are additional pulses that decrease in amplitude with time. These pulses again represent the energy received by the transducer 10 from the front and rear surfaces of workpiece 26, the sound energy reflecting back and forth between the front and rear surfaces of the workpiece before it leaves the same and reaches the transducer.

Beneath the train of video pulses in FIG. 2 is a curve B that shows the output of integrating circuit 18. The signal presented to 18 by 16 is a video waveform having timing logic. Using this waveform and logic 18 computes the area of each pulse it receives and adds the same to the area of the next succeeding pulse to provide a function that increases stepwise to a maximum value for a period of time determined by the logic of 18. This period of time is chosen to allow the occurrence and receipt of the number of video pulses sufficient to provide the maximum signal of FIG. 2. 18 then sets itself to zero to await another set of pulses from the transducer. Just before 18 sets itself to zero, however, it transfers the integrated value to holding circuit 22. 22 is essentially an analogue memory that holds the value from 18 for future use in the system of the invention in a manner presently to be explained.

In systems employing more than one transducer, an analogue memory can be provided for each transducer. In the case where say two transducers are ganged together, only one analogue memory is necessary since when one transducer is leveled the other one will be leveled also. The contents of each hold circuit then can represent the two transducers and be available for examination. In the case where several transducers or transducer pairs are employed, a hold circuit 22 can be provided for each transducer or each pair thereof. The hold circuits can receive their inputs from a single integrating circuit 18, and a multiplexing arrangement (not shown) can operate to sequentially sample the output of each transducer, present each to the integrating circuit and sequentially provide and update each hold circuit with the information from the integrating circuit. In addition, such multiplexing permits the calibration of each transducer in a manner explained hereinafter.

FIG. 3 shows diagrammatically a system that utilizes the integrated video of FIGS. 1 and 2 to control the angle of a search unit (comprised of two transduceers 10A and B ganged together) and that performs certain other functions described below.

In order to obtain the best possible readings in detecting a discontinuity in a workpiece, as explained earlier, it is necessary to maintain the working face of a sound transducer (or transducers) parallel to the workpiece. The system of FIG. 3 provides this in the following manner.

The output of only transducer B in FIG. 3 is presented to instrument 24 and to a system microcomputer 58, as A and B are ganged together. As mentioned earlier, the output of 10B is first amplified by 30 and "maintained" by line driver 32.

Still referring to FIG. 3, the output of integrator 18 in instrument 24 is connected to an angulation computer circuit 34 via a data bus or cable 36. 34 is a circuit device, such as a plug-in computer card, capable of receiving the analogue output of integrator 18, converting it to digital form and ordering a change in the angle of transducers 10A and B (relative to workpiece 26) when 34 perceives a reduction in signal level from 18 and 22.

34 has stored therein a value representing the maximum signal strength from 18 and 22.

A reduction in signal strength occurs, for example, when the angle of the transducers is such that some of the reflection from the front and rear surfaces of the workpiece is lost. In FIG. 2, this would be a loss or reduction in size of the third spike or pulse in the A series of pulses, thereby resulting in direct reduction in the strength of the integrated value of signal B in FIG. 2.

The digital output of circuit 34 is connected via a data bus or cable 38 to three circuit means generally designated 40 in FIG. 3 designed to control two "angulation" motors 42 and 44 and one "vertical positioning" motor 46 in FIG. 3. Circuit means 40 can be a small plug-in card containing appropriate components for utilizing the output of 34, and connected to order incremental movement of the motors. The plug-in card and motors are commercially available from such manufacturers as Superior Electric Company of Bristol, Connecticut, though other control devices and motors can be used.

As seen schematically in FIG. 3, the transducers 10 are mounted at the lower end of a vertical shaft 48, the upper end of which is attached to a structure 50 adapted to support motors 42 and 44. The lower end of shaft 48 supports transducers A and B on a platform 51 and in a manner that allows angular movement thereof about two, mutually perpendicular (xy) axes that are parallel to workpiece 26. Preferably, shaft 48 is hollow so that it can accommodate leads that electrically connect the transducers to the associated circuit devices of 12 and 30, and mechanical means (not shown) for moving the transducers about the mutually perpendicular axes. Motors 42 and 44, for example, can be linked to platform 51 by two screw mechanisms located in the hollow of shaft 48.

Motor 46, as indicated in FIG. 3, is mechanically connected to shaft 48 by a threaded screw device generally designated by numeral 52. Linear bearing devices (not shown) support the shaft to permit vertical movement thereof via screw 52.

The operation of the system, as thus far described, is as follows. Angulation computer circuit 34 is programmed to examine the integrated video output from 18 and 22 to determine the amount of signal being sequentially forwarded from the transducers. If transducer 10B is not parallel to workpiece 26, the amount of sound reflected from the workpiece to the transducer is less than maximum. The output of the transducer, in turn, is less than maximum such that the integrated value provided by 18 and held in 22 is less than the maximum value known to circuit 34. 34 immediately makes this comparison and outputs a digital signal to 40 which, in turn, outputs a signal to motors 42 and 44. If the parallel relationship is off in only one direction, say in the direction of the x axis, only the "x" motor (of 42 and 44) will step incrementally to rotate platform 51 to effect a parallel relationship of transducers 10A and B to the workpiece until signal strength from sample hold circuit 22 is again maximum. When this happens, 34 stops outputting instructions to 40.

Another critical aspect of sonic flaw detection is the depth or thickness of the water path between the transducer and the workpiece. Water path distance must be kept at an optimum value to provide accurate detection of discontinuities and an inspection process consistent with the calibration of the system, as described hereinafter.

Computer circuit 34 in the present invention is provided with the capability of measuring the distance of the water path between the transducers and workpiece, and of ordering motor 46 to raise or lower the transducers depending upon the results of certain calculations made by 34.

The travel time of sound in water is a known datum, and the water path distance for optimum performance of the system is also a known datum. This later datum, preferably in the form of a fixed time period representing the time it takes for sound to travel the optimum distance in water, is stored in 34. The computer then periodically measures the time period between the occurrence of the pulse that energizes the transducer and the receipt of echo by the transducer from the front surface of the workpiece. 34 compares this time period, which has traveled twice through the water (in going to and from the transducer), to the datum representing the optimum travel time. If there is a difference between the two, the computer outputs this difference to controller 40. 40, in turn, provides the appropriate instructions for motor 46, 46 lowering or raising shaft 48 until the time period being monitored by 34 equals that of the stored datum of optimum time. When this occurs, 34 ceases to output instructions to 46.

The system of the invention can be calibrated by use of a standard or test object 53 (FIG. 4) of a thickness and composition that are known and that corresponds to that of the material of the workpiece to be examined. The accuracy of the test object is authoritatively established such as by the National Bureau of Standards.

Such a test object 53 is shown in perspective in FIG. 4. More particularly, 53 comprises a piece of material of the above known thickness and composition, and of a breadth sufficient to encompass the width of a plurality of sonic transducers, four such transducers being shown in FIG. 4. Test object 53 has a narrow groove or slot 54 provided in one (lower) face thereof to provide a precise, known thickness of material from the top surface to the reflecting surface of the slot and a precise ultrasonic response from the reflecting surface of the slot. The test object is placed in the water 28 of FIG. 3, with slot 54 facing away from the four transducers. The transducers, which comprise two search units labeled 10 and 10' in FIG. 4 are moved in the water sequentially over the test object, as indicated by arrow 56. When water 10' is positioned over the test object, it is leveled using the procedure described above in connection with the examination of workpiece 26. In addition, before the transducers are calibrated, the thickness of the water path between the transducers and test object 53 is measured by circuit 34, and the transducers vertically adjusted if the water thickness is not optimum.

When each transducer is located over 54 and pulsed by pulser 12, the transducer produces output pulses that are monitored by a process control, microcomputer 58 (FIG. 3) of the detection means of the system (not otherwise shown), which is programmed to compare the amplitue of pulses produced by detector 17 and measured by peak detector circuits (not shown) (which provides 58 only with the maximum amplitude pulses from 16 in a well-known manner) to the known response of the test object, the datum of this response being stored in 58. If the amplitude of the pulses from detector 17 is not the same as the stored datum of the test object, 58 orders adjustment in the gain of amplifier 30 until the output of 16 equals the stored datum and known ultrasonic response value of the test object.

The computer 58 is a digital device while the amplifiers 16 and 30 are analogue devices. For this reason computer 58 can provide internal analogue to digital conversion for the output of 6 and digital to analogue conversion for the adjusting signal sent to 30.

With each transducer calibrated in the above manner, the transducers are now ready to be leveled and vertically adjusted over a workpiece to be examined. This is done individually for each transducer or search unit of the system if more than one transducer or search unit is employed.

While the invention has been described in terms of preferred embodiments, the claims appended hereto are intended to encompass all embodiments which fall within the spirit of the invention.

What is claimed is:

1. A method of maintaining parallel relationship between the working face of a sound transducer and a planar surface of an object under examination by the transducer and by circuitry electrically associated with the transducer, the method comprising the steps of:
   providing a transducer and associated circuitry,
   placing the working face of the transducer in a position that is adjacent to but spaced from the planar surface of the object,
   providing a layer of liquid between the working face of the transducer and the object,
   energizing the transducer such that sound energy is directed into and reflected from the object after passing through the layer of liquid, the sound energy reflected from the object being received at the working face of the transducer and the transducer produces a train of electrical pulses in response to the reflected energy received by it from the object,
   integrating said train of pulses to provide an analogue signal that is proportional to the total amount of sound energy received by the transducer, the amount of sound energy received by the transducer being maximum when the face of the transducer and the planar surface of the object are essentially parallel to each other, and
   utilizing the analogue signal to maintain parallel relationship between the working face of the transducer and the planar surface of the object.

2. The method of claim 1 in which the integrating step includes integrating pulses representing sound energy reflected from both front and rear surfaces of the object.

3. The method of claim 1 in which the step of utilizing the analogue signal includes the step of moving the transducer in response to the signal about x and/or y axes, said axes being parallel to the planar surface of the object under examination.

4. The method of claim 1 including the step of directing the analogue signal to a computer, the computer being effective to automatically control the angle of the transducer with respect to the object under examination in response to the magnitude of the analogue signal.

5. The apparatus of claim 1 in which the means for utilizing the analogue signal includes a computer, the computer being effective to automatically control the angle of the transducer with respect to the object under examination in response to the magnitude of the analogue signal.

6. Apparatus for maintaining parallel relationship between the working face of a sound transducer and a planar surface of an object under examination by the transducer and by associated electrical circuitry, the apparatus comprising:
   a sound transducer disposed adjacent to but spaced from the planar surface of the object,
   electrical circuitry for energizing the transducer and for receiving electrical pulses from the transducer in response to sound echoes from the object,
   said circuitry including means to integrate said pulses to provide an analogue signal that is proportional to the total amount of echo energy received by the transducer from the object under examination, and
   means for utilizing said analogue signal to maintain the parallel relationship between the working face of the transducer and the planar surface of the object under examination.

7. A method of calibrating a sound transducer and associated circuitry adapted to examine the integrity of a workpiece having front and rear surfaces, the method including the steps of:
   placing a search unit comprised of at least one sound transducer in spaced, noncontacting relationship with a test object having a planar surface and a precisely determined sound response when it receives sound energy from the transducer, the search unit being mechanically supported to move about axes that are parallel with the planar surface of the test object,
   providing a layer of liquid between the transducer and the test object,
   energizing the transducer,
   leveling the transducer so that its working face is parallel with the planar surface of the test object, said leveling step including the step of integrating a train of pulses produced by the transducer to thereby provide an analogue signal that is proportional to the total amount of sound energy received by the transducer,
   using said analogue signal to maintain the transducer in a level position, and
   adjusting the sensitivity of the circuitry associated with the transducer after it is in parallel relationship with the planar surface of the test object to obtain a response from the circuitry that is the same as that of the precisely determined response of the test object.

8. The method of claim 7 in which sound energy is reflected from the test object to the transducer, the transducer producing an output signal in response to the reflected energy, the method including the additional steps of:
   directing the signal to an amplifier of the circuitry associated with the transducer, and
   adjusting the gain of the amplifier in response to the magnitude of the output signal from the transducer until the amplifier provides an output that corresponds to the known response of the test object.

9. The method of claim 8 in which the output of the amplifier is a video signal employed for video presentation to operating personnel, the adjusting step including the step of computing a correct gain adjustment by comparing the video signal with a signal stored in a digital computer, the stored signal representing the precisely determined response of the test object.

10. The method of claim 7 in which the search unit comprises two sound transducers having respective circuitry associated therewith, and the test object has a grooved surface providing the precisely determined sound response, the method including the steps of:

leveling both transducers so that the working faces thereof are parallel with the planar surface of the test object, locating each transducer over the surface of the test object opposite the grooved surface, and adjusting the circuitry of each transducer after the parallel relationship of each transducer with the test object is effected to obtain the precisely determined response from the test object for each transducer.

11. Apparatus for calibrating a sound transducer and circuitry associated therewith, the apparatus comprising:

at least one transducer having a working face and associated circuitry for examining the integrity of a workpiece, a test object having a planar surface and a precisely calibrated sound response when sound energy is directed into the object, means for locating the working face of the transducer in spaced, noncontacting relationship with a workpiece and with the test object, circuit means for integrating pulses produced by the transducer, and for providing therefrom an analogue signal, means for moving the transducer about axes that are parallel with the planar surface of the test object in a manner that establishes parallel relationships between the working face of the transducer and the planar surface of the test object in response to the analogue signal, and means for adjusting the sensitivity of the circuitry after parallel relationship is established between the transducer and test object until the response of the transducer and circuitry is the same as the precisely calibrated response of the test object.

12. The apparatus of claim 11 in which the transducer produces an output signal in response to sound energy reflected to it from the test object, and the circuitry associated with the transducer includes an amplifier for amplifying the output of the transducer, the amplifier, in turn, producing an output signal in response to the signal from the transducer, the apparatus including:

means for comparing the output of amplifier with the precisely calibrated response of the test object when the object receives sound energy from the transducer, and for changing the gain of the amplifier in response to any difference occurring between the amplifier output and the calibrated response of the test object.

* * * * *